United States Patent [19]
Field

[11] Patent Number: 6,006,750
[45] Date of Patent: Dec. 28, 1999

[54] POSITION SENSING SYSTEM AND METHOD FOR USING THE SAME

[75] Inventor: Steven E. Field, Grand Rapids, Mich.

[73] Assignee: Medtronic, Inc., Minneapolis, Minn.

[21] Appl. No.: 08/637,972

[22] Filed: Apr. 30, 1996

[51] Int. Cl.⁶ .................................................. A61B 5/00
[52] U.S. Cl. ..................................... 128/653.1; 128/657
[58] Field of Search ..................... 128/754, 771, 128/662.05, 657, 749, 653.1, 653.2; 606/1

[56] References Cited

U.S. PATENT DOCUMENTS

| | | | |
|---|---|---|---|
| 3,556,079 | 1/1971 | Omizo | 128/2 |
| 4,407,294 | 10/1983 | Vilkomerson | 128/662.05 |
| 4,907,252 | 3/1990 | Aichinger et al. | |
| 5,158,084 | 10/1992 | Ghiata | 128/657 |
| 5,305,203 | 4/1994 | Raab | |
| 5,365,447 | 11/1994 | Dennis | |
| 5,377,678 | 1/1995 | Dumoulin et al. | |
| 5,446,548 | 8/1995 | Gerig et al. | |

OTHER PUBLICATIONS

Ghiatas™ Beaded Breast localization Wire Set Product Brochure, Copyright 1994, Medtronic, Inc.

The Ghiatas™ Beaded Localization Wire Product Brochure, Copyright 1994, Medtronic, Inc.

"Mammography, Modified Localization Wire for Breast Lesions," by Abraham A. Ghiatas et al., Eur. Radiol. 2, 1992.

*Primary Examiner*—Marvin M. Lateef
*Assistant Examiner*—Derrick Fields
*Attorney, Agent, or Firm*—Foley & Lardner

[57] ABSTRACT

A positioning system for marking a specified location within tissue includes a hollow needle and a localization wire adapted for insertion through the hollow needle and into the specified location. A transmitter is connected to the localization wire for transmitting a signal through the tissue so that the specified location can be accurately determined when the transmitter is placed thereat. A method of marking a specified location within tissue includes inserting a hollow introducer needle into the tissue until a tip of the needle reaches the specified location. A localization wire having a transmitter is then inserted into the hollow needle until the transmitter is positioned at the specified location. The hollow needle is then removed from the tissue such that only the localization wire and transmitter remain embedded therein. The transmitter is subsequently located by probing an outside surface of the tissue with a receiver until the maximum signal strength is achieved. The maximum signal strength is directly indicative of the transmitter's position at the specified location.

12 Claims, 3 Drawing Sheets

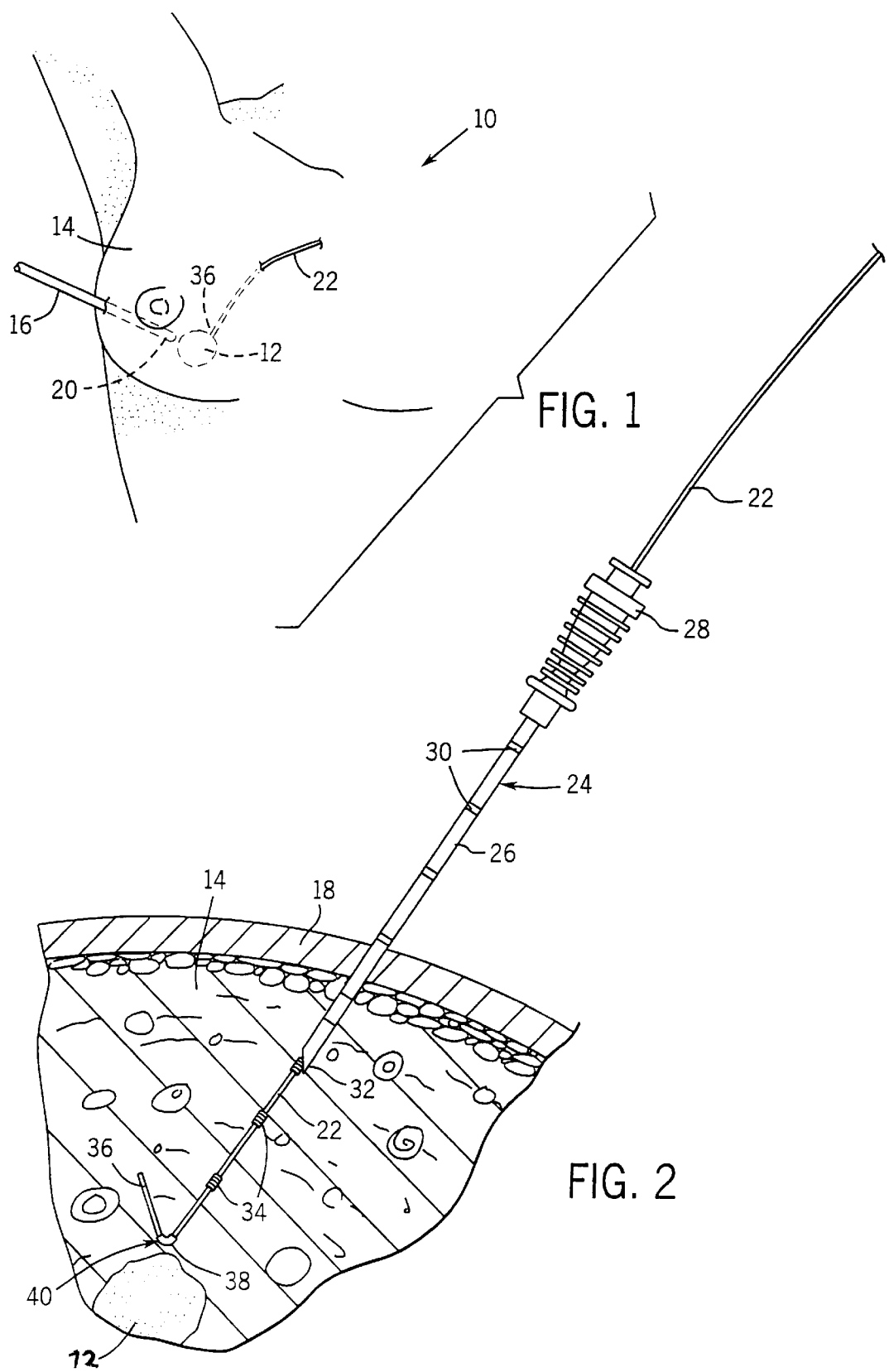

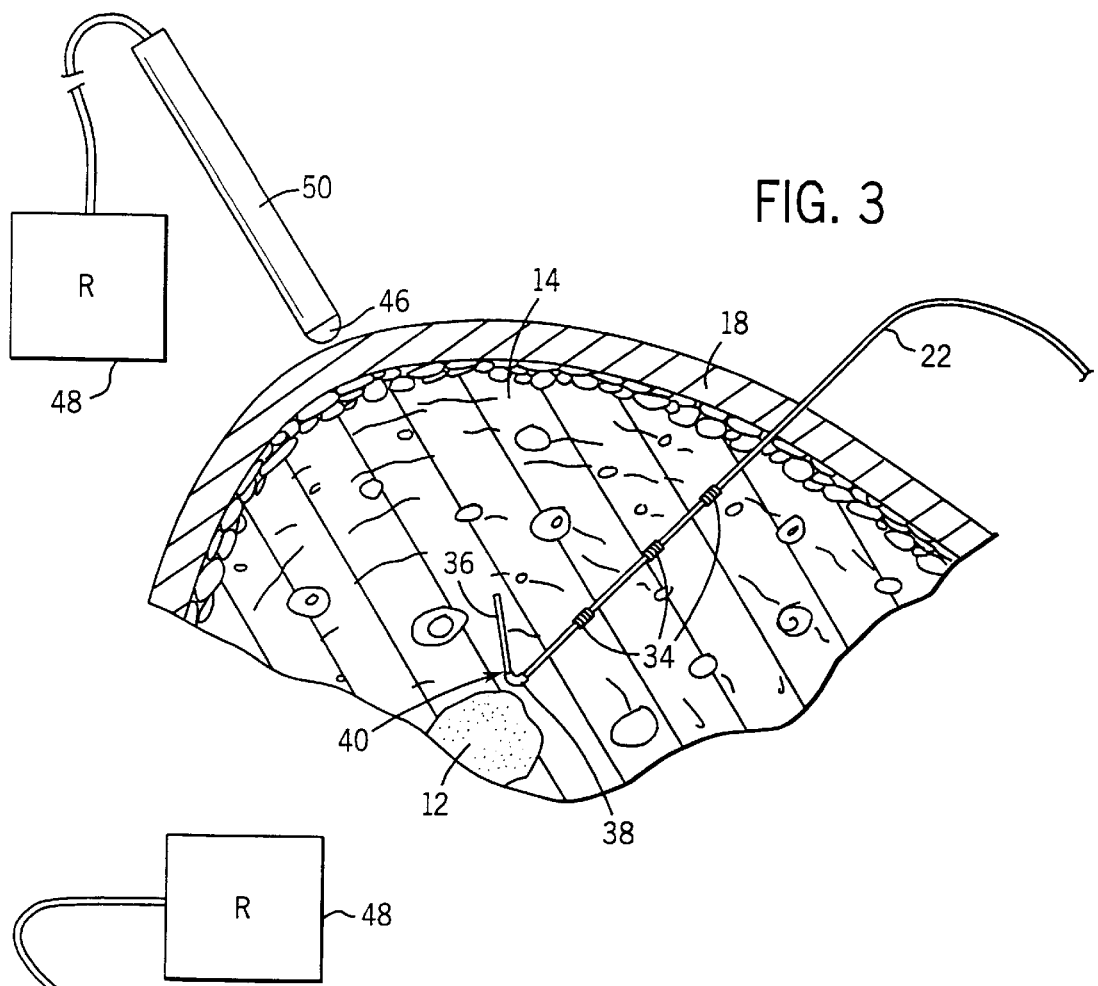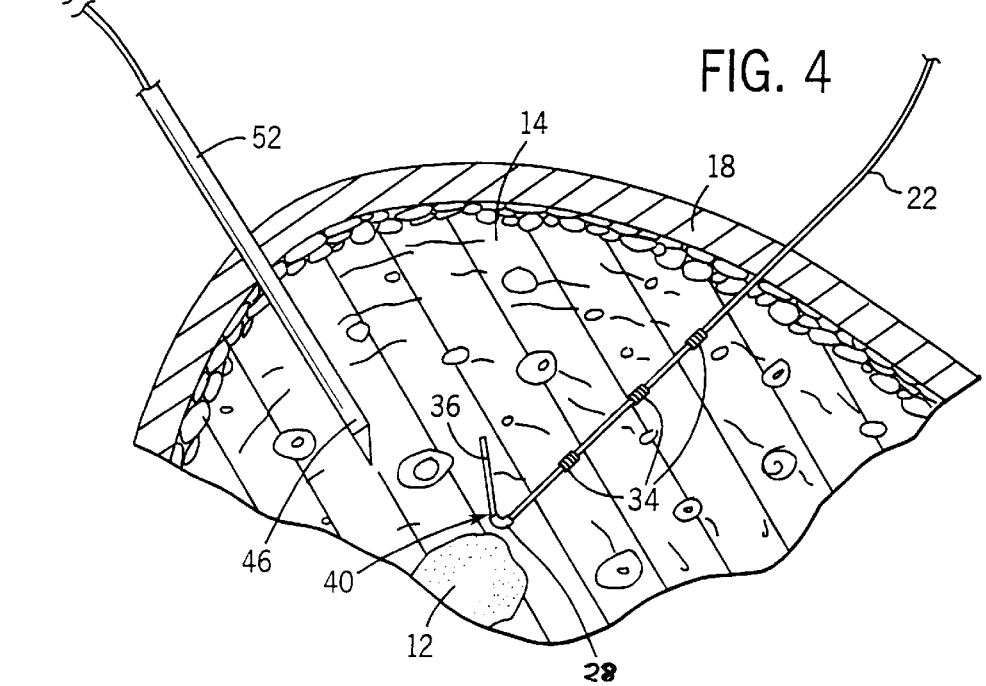

POSITION SENSING SYSTEM AND METHOD FOR USING THE SAME

BACKGROUND OF THE INVENTION

1. Field of the Invention

This invention relates to surgical procedures and, more particularly, to a position sensing system or a guidance system adapted to assist a surgeon in locating a predetermined position once a transmitter or receiver is surgically implanted.

2. Description of the Related Art

Localization wires have long been used to assist surgeons in identifying the position of certain tissue inside the human body. For example, localization wires are often implanted for the purpose of guiding a surgeon to a tumor or lesion for surgical excision.

In one known application of the localization wire, the distal tip of a hollow needle is inserted into body tissue and positioned so that the distal tip of the needle is immediately adjacent to the desired tissue or lesion. Next, the localization wire is inserted through the hollow needle until the distal tip of the wire is positioned in or immediately adjacent to the lesion. Finally, the needle is withdrawn, leaving the wire in the appropriate position. The needle and wire are typically positioned by a radiologist using conventional methods and equipment. Preferably, a barb or tine is formed at the end of the wire for holding the wire in position. Once the wire is properly positioned, the surgeon uses the wire as a guide for the biopsy or excision of the tissue adjacent the end of the wire. The surgeon can follow the wire to the lesion for excision. However, this procedure oftentimes creates more cicatricial tissue than is necessary. In an effort to minimize cicatrix formation, surgeons have adopted the technique of inserting the biopsy needle at a location remote from the localization wire.

It is known to provide enhancements on the wire and needle to assist the users in positioning the wire and needle and also identifying the depth of insertion of the wire, as seen in U.S. Pat. Nos. 5,158,084 and 5,490,521. Despite the known enhancements on the wire, it is still difficult for surgeons to accurately locate the distal tip of the positioned localization wire without causing excess trauma to the surrounding tissue.

SUMMARY OF THE INVENTION

The positioning system according to the invention overcomes the problems of the prior art by providing means for the surgeon to accurately locate the position of at least a portion of a localization wire or a previously implanted transmitter or receiver with a minimum amount of trauma to the surrounding tissue.

According to one aspect of the invention, a positioning system for marking a specified location within tissue includes a hollow needle and a localization wire adapted for insertion through the hollow needle and positioning at a specified location. A transmitter is provided on the localization wire which is adapted to transmit a signal through the tissue so that the specified location can be accurately determined when the transmitter is placed thereat. An internal or an external receiver is used by the surgeon to locate the wire tip and lesion adjacent thereto.

In another embodiment, a positioning system for marking a specified location within tissue includes a hollow needle and either a transmitter or receiver which is selectively received in the needle. The distal tip of the needle is inserted into the body tissue and positioned immediately adjacent the lesion. The needle is actuated to eject either a transmitter or a receiver therefrom. Next, the needle is withdrawn therefrom, leaving the transmitter or receiver in place, adjacent the desired tissue. With this structure, the surgeon can then use a probe to guide the surgeon directly to the transmitter for excision of the lesion.

In a further aspect of the invention, a method of marking a specified location within tissue includes inserting a hollow localization needle into the tissue until a tip of the needle reaches the specified location. A localization wire having a transmitter is then inserted into the hollow needle until the transmitter is positioned at the specified location. Alternatively, a transmitter is ejected from the needle and remains adjacent the specific tissue. The hollow needle is then removed from the tissue such that only the localization wire and transmitter remain embedded therein. The transmitter is subsequently located by probing an outside surface of the tissue with a receiver until the maximum signal strength is achieved. The maximum signal strength is directly indicative of the transmitter's position at the specified location.

BRIEF DESCRIPTION OF THE DRAWINGS

The invention will now be described with reference to the drawings in which:

FIG. 1 is a top view of a localization wire and biopsy needle in use during a biopsy procedure according to the present invention;

FIG. 2 is a partial, cross-sectional view of body tissue with the localization wire and needle during positioning of the wire;

FIG. 3 is a partial, cross-sectional view of body tissue with the localization wire in position and use of an external probe for identifying the position of the lesion and the distal tip of the wire;

FIG. 4 is a partial, cross-sectional view similar to FIG. 3 showing use of an internal probe for identifying the position of the lesion and the distal tip of the wire.

DETAILED DESCRIPTION OF THE PREFERRED EMBODIMENTS

Figure 5:
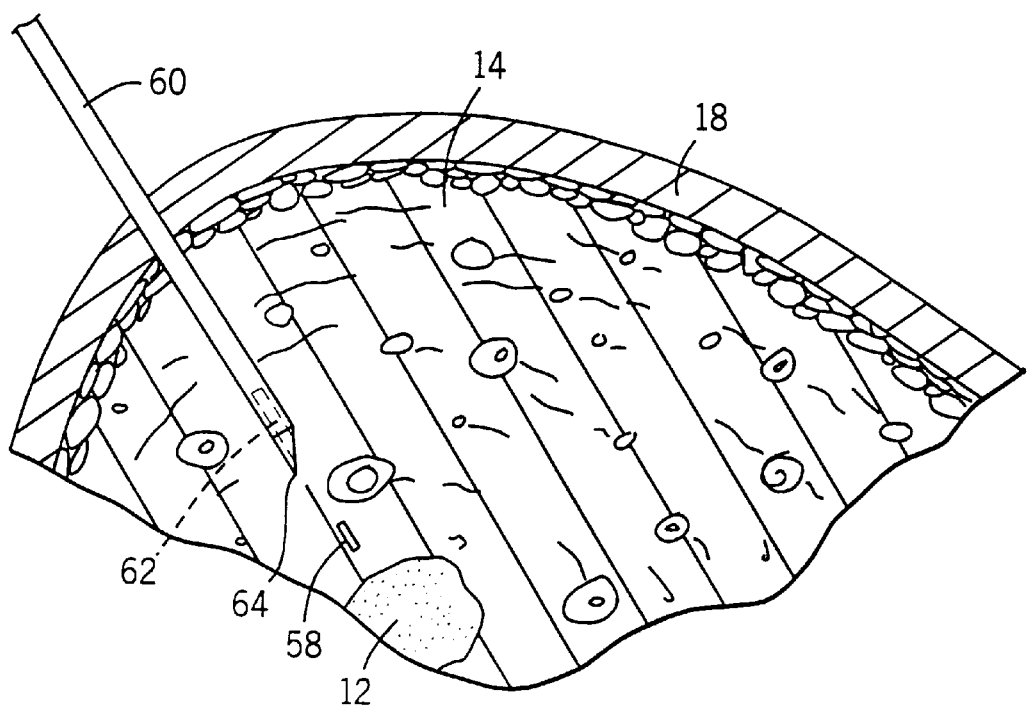
FIG. 5 is a partial cross-sectional view similar to FIG. 4 showing a second embodiment of the positioning system according to the invention.

Referring now to FIGS. 1 and 2, a patient 10 having a tumor or lesion 12 within a breast 14 to be surgically excised is shown. When the tumor 12 is discovered, a biopsy is usually recommended to determine if the tumor is benign or malignant. In excisional biopsy, the surgeon cuts the surrounding tissue to reach the tumor and then removes or excises the tumor, in whole or in part. Until recently, if the tumor could not be felt through the skin, the surgeon would have to rely on his knowledge of anatomy and personal experience to locate its position. The provision of a localization wire 22 according to the present invention facilitates exact positioning of the incision for retrieving tissue samples.

In the first embodiment as seen in FIGS. 1–4, a hollow introducer needle 24 includes a hollow needle body 26 connected to a hollow handle or hub 28 at one end and a sharpened tip 32 provided at the other end. A plurality of depth marks 30, typically spaced at one centimeter intervals, are preferably provided on the needle body 26 between the sharpened tip 32 and hub 28. A flexible localization wire 22 is sized for reception into the hollow needle 24 and includes a solid flexible wire that terminates at one end with a tyne or barb 36. A plurality of depth marks 34 may also be provided on the wire 22 at spaced intervals from the barb 36. Preferably, the spacing between intervals is one centimeter.

As seen in FIGS. 3 and 4, means are provided on the wire 22 for assisting the surgeon in locating the distal tip of the wire which is positioned in or adjacent to the lesion. In the preferred embodiment, a micro transmitter 38 is provided at the juncture of the barb 36 and the body of the wire 22. The transmitter 38 is adapted to emit a signal which is received by a receiver 46 provided on a receiving unit 48. Preferably, the receiver 46 is mounted at the end of a hand-held probe 50 which can be manipulated around the breast tissue 14 to assist the surgeon in determining the position of the lesion 12. The receiver 46 can be mounted on a probe 50 which is used only externally as seen in FIG. 3. Alternatively, as seen in FIG. 4, the receiver 46 can be provided on an internal probe or needle 52 which is inserted into the breast tissue during the excision process.

While the preferred embodiment shows the transmitter 38 on the wire 22 and the receiver on the probe, this orientation can be easily reversed so that the receiver is positioned on the wire and the transmitter is on the probe. With this orientation, means must be provided for conducting the received signal from the tip of the wire 22 back to the receiving unit. Possible suitable structures include electrical conductors extending from the wire 22 or transmission of the signal from the receiver on the wire to an external monitoring device.

With the significant advances in technology, a wide variety of transmitters and receivers suitable for use according to the invention are available, or will be developed in the future. The transmitter and receiver can be based on ultrasonic principles. Alternatively, radio or microwave signals could also be utilized in practicing the invention. Any signal adapted to be transmitted and received locally falls within the scope of the invention.

In operation, the pre-operative localization of a breast lesion 12 utilizing a localization wire 22 is performed by a radiologist. The radiologist first determines the location and depth of the lesion 12 through conventional techniques such as x-ray or ultrasound imaging. A hollow introducer needle 24 is inserted into the breast 14 and directed toward the lesion. The needle is preferably inserted parallel to the chest wall to reduce possible risk of pneumothorax. The depth markings 30 on the needle in conjunction with the x-ray and ultrasound equipment permit the radiologist to position the needle point 32 into or immediately adjacent the breast lesion 12. The needle position is then confirmed through x-ray and/or ultrasound. If the needle point misses the lesion, the needle is repositioned and its placement is reconfirmed. The localization wire 22 is then inserted into the hollow needle 24 until the barb 36 at the end of the localization wire is adjacent the end of the needle tip 32. The needle 24 is then withdrawn until the end of the wire 22 is clear of the needle tip 32. The barb 36 is biased outwardly into the lesion or surrounding tissue to hold the wire 22 in place. The needle is typically removed from the tissue leaving the wire positioned near or in the lesion.

Once the wire 22 is properly positioned, the patient is ready for the appropriate surgical excision or biopsy. Utilizing the external hand probe 50 of the first embodiment seen in FIG. 3, the surgeon manipulates the probe around the breast 14. As the probe is maneuvered around breast 14, the receiver 46 receives the signal from the transmitter 38 and the signal is interpreted by the receiving unit 48. Utilizing the external hand probe 50 and the signals from the transmitter 38 as interpreted by the receiving unit 48, the surgeon can effectively map out the position of the distal tip of the wire 22 and adjacent lesion.

In the alternative embodiment seen in FIG. 4 where an internal probe 50 is utilized, the surgeon inserts the probe 52 while the receiver 46 receives the signal from the transmitter 38. The receiving unit 48 will interpret the movement of the internal probe 52 thereby guiding the movement of the probe 52 closer and closer to the transmitter 38 and the adjacent lesion 12. In essence, the cooperation of the transmitter and the receiver will lead the surgeon directly to the tumor eliminating any guess work or excessive trauma to the surrounding tissue.

Once the internal probe or hand-held probe has been used to properly locate the lesion 12, the surgeon can perform the necessary surgical excision. Finally, the localization wire 22 is removed in the conventional manner.

Although the localization wire according to the present invention has been described for use with surgical excision of breast lesions, the wire may be used in any other procedure throughout the body wherein a certain position or tissue within the body is pre-located and then subsequently accessed by other means. For example, the localization wire may be used in performing lung biopsies.

FIG. 5 depicts a second embodiment of the positioning system. In this embodiment, a stand alone transmitter 58 is implanted immediately adjacent the lesion 12 through the use of a conventional hollow needle 60. Initially, the transmitter 58 is received in a suitable recess 62 provided in the sharpened, distal tip 64 of the needle 60. Preferably, the distal tip 64 has some form of echogenic enhancement means provided thereon to assist the radiologist in properly positioning the tip 64. Once the tip 64 is positioned in or immediately adjacent the lesion 12, then a plunger telescopically received inside the hollow needle 60 is actuated to eject the transmitter 58 from the needle 60. Once the transmitter 58 has been discharged from the needle 60, then the needle is withdrawn. With the transmitter positioned adjacent or in the lesion, then the surgeon can use either the external probe 50 as seen in FIG. 3 or the internal probe 52 as seen in FIG. 4 for properly locating the transmitter 58 and the lesion 12.

Reasonable variation and modification are possible within the spirit of the foregoing specification and drawings without departing from the scope of the invention.

The embodiments for which an exclusive property or privilege is claimed are defined as follows:

1. A surgical guidance system for directing a surgeon to a desired position in tissue within a body comprising:

a localization wire having proximal and distal ends, the distal end being adapted to be inserted into body tissue and positioned at a desired position;

a surgical tool adapted to be inserted into said body and maneuvered around the localization wire; and one of a transmitter element and a receiver element being provided on the localization wire, the other of the transmitter element and receiver element being provided on the surgical tool at a position so that said other of the transmitter element and receiver element is adapted to be inserted into said body, the transmitter element being adapted to emit a signal and the receiver element being adapted to receive the signal; and a receiving unit electrically connected to the receiver element and adapted to interpret said signal;

whereby the guidance system can be used in accurately leading a surgeon to a desired location when the distal end of the wire is positioned adjacent the desired tissue and the transmitter and receiver are utilized to determine the position of wire with respect to the probe.

2. A surgical guidance system according to claim 1 wherein the transmitter is provided on the localization wire.

3. A surgical guidance system according to claim 2 wherein the transmitter is provided on the distal end of the wire.

4. A surgical guidance system according to claim 2 wherein the distal end of the wire has a barb formed thereon and the transmitter is positioned immediately adjacent the barb.

5. A surgical guidance system according to claim 1 wherein the surgical tool comprises a biopsy needle.

6. A surgical guidance system for directing a surgeon to a certain position in a body comprising:
   a hollow introducer needle adapted to be inserted into the body;
   a probe adapted to be surgically received inside the body and maneuvered with respect to the introducer needle;
   one of a transmitter element and a receiver element being selectively mounted to the introducer needle, the other of the transmitter element and receiver element being provided on the probe, the transmitter element being adapted to be positioned adjacent the desired tissue and to emit a signal, the receiver element being adapted to receive the signal; and
   a receiving unit electrically connected to the receiver element and adapted to interpret said signal;
   whereby the guidance system can be used in accurately leading a surgeon to a desired location inside the body when said one of the transmitter and receiver element is positioned adjacent the desired location and the transmitter and receiver are utilized to determine the position of the probe with respect to the desired tissue.

7. A surgical guidance system according to claim 6 wherein the probe comprises a biopsy needle.

8. A surgical guidance system according to claim 7 wherein the receiver is provided on the biopsy needle.

9. A surgical guidance system according to claim 6 wherein the wherein the transmitter is selectively mounted to the introducer needle.

10. A surgical guidance system according to claim 6 wherein the transmitter is selectively mounted to the distal end of the introducer needle.

11. A method of guiding a surgeon to a desired location in a body comprising the steps of:
    providing a localization wire having proximal and distal ends;
    providing one of a transmitter and receiver on the localization wire;
    positioning the distal end of the localization wire inside the body immediately adjacent the desired location;
    providing a probe having a portion adapted to be inserted into said body and maneuvered with respect to the localization wire, the other of the transmitter and receiver being provided on said portion of the probe;
    emitting a signal from the transmitter;
    receiving the signal with the receiver and interpreting the signal in order to determine the position of the transmitter with respect to the receiver and;
    inserting said portion of the probe into the body and maneuvering the probe with respect to the localization wire;
    whereby the position of the desired location can be determined through manipulation of the probe with respect to the localization wire and interpretation of the signals transmitted and received by the transmitter and receiver.

12. A method of guiding a surgeon to a desired location according to claim 11 wherein the localization wire is positioned by inserting one end of a hollow introducer needle into the body and inserting the wire through the needle so that the distal end of the wire is adjacent the desired location and then slidably removing the introducer needle while retaining the localization wire at the desired location.

* * * * *

UNITED STATES PATENT AND TRADEMARK OFFICE
CERTIFICATE OF CORRECTION

PATENT NO. : 6,006,750
DATED : Dec. 28, 1999
INVENTOR(S) : Field

It is certified that error appears in the above-identified patent and that said Letters Patent is hereby corrected as shown below:

Col. 6, line 2, delete the first occurrence of "wherein the".

Signed and Sealed this

Eighth Day of August, 2000

Attest:

Q. TODD DICKINSON

Attesting Officer

Director of Patents and Trademarks